United States Patent [19]
Sakai

[11] Patent Number: 5,453,420
[45] Date of Patent: Sep. 26, 1995

[54] FOOD PRESERVATIVE AND PRODUCTION THEREOF

[76] Inventor: Isao Sakai, 2-11, Nishiogi-minami 1-chome, Suginami-ku, Tokyo, Japan

[21] Appl. No.: 109,315

[22] Filed: Aug. 19, 1993

[30] Foreign Application Priority Data

Sep. 2, 1992 [JP] Japan .................. 4-257565

[51] Int. Cl.$^6$ .................. A61K 38/00; A23B 7/10
[52] U.S. Cl. .................. 514/12; 424/195.1; 514/143; 426/486; 426/488; 426/615; 426/638
[58] Field of Search .................. 514/12, 143; 426/656, 426/615, 638, 488, 486; 424/195.1

[56] References Cited

FOREIGN PATENT DOCUMENTS

| | | |
|---|---|---|
| 63-10976 | 5/1988 | Japan . |
| 0210717 | 4/1990 | Japan . |
| 3215419 | 9/1991 | Japan . |
| 4-5211 | 1/1992 | Japan . |

*Primary Examiner*—Howard L. Schain
*Assistant Examiner*—Lynn Touzeau
*Attorney, Agent, or Firm*—Martin Smolowitz

[57] ABSTRACT

Garlic essence is produced by extracting garlic with ethanol and deodorized with phytic acid, added either during or after the extracting step. The garlic essence exhibits outstanding antibacterial action when added to or sprayed onto foods. It is used alone or in combination with ε-polylysine in the amount of 1–256 μg/ml.

10 Claims, No Drawings

FOOD PRESERVATIVE AND PRODUCTION THEREOF

BACKGROUND OF THE INVENTION

The present invention relates to a food preservative and a process for producing the same, and more particularly, to a food preservative to inhibit the propagation of bacteria by the aid of a vegetable alkaloid and to a process for producing the same.

It is known that horse radish for Sushi functions as a preservative because it contains sinigrin (a vegetable alkaloid), which, on decomposition by the enzyme myrosinase, becomes mustard oil (allyl isothiocyanate), which exhibits the antibacterial action. It is also known that garlic contains allicin ($C_6H_{10}OS_2$), which has the antibacterial action. It is also known that ε-polylysine, which is an amino compound formed from L-lysine through the peptide bond between the α-carboxyl group and the amino group at the ε position, is effective in inhibiting the propagation of lactic acid bacteria, *Escherichia coli*, and *Staphylococcus aureus*. Hence, it is used as a food additive. In general, ε-polylysine is highly effective and easy to use; however, there are some foods for which it is not necessarily effective. Edible meat is an examples of them.

There are a large variety of vegetable alkaloids, some of which are toxic and others are edible. The vegetables that yield edible alkaloids include red pepper (capsanthin), common ginger root (zingerone and shogaol), pepper (chavicine), horse radish (sinigrin), mustard (sinaibin and sinigrin), and garlic (allicin). They are all known as spices. Extracting vegetable alkaloids from spices is not economical, except for garlic. Garlic yields a large amount of large bulbs capable of easy processing; however, it suffers the serious disadvantage of giving off a characteristic odor, and the production of allicin is accompanied by this odor. Garlic derives its odor and pungent taste from garlic oil, which contains allyl sulfide, allyl disulfide, allylpropyl disulfide, and allyl trisulfide. These sulfides give off the characteristic odor when they are decomposed into disulfide and sulfur dioxide by the alkali in garlic. This decomposition is accompanied by the formation of alliin ($C_6H_{11}NO_3S$), and alliin is subsequently decomposed into allicin ($C_6H_{10}OS_2$) by the enzyme alliinase. In other words, alliin dominates allicin in garlic, and hence it is difficult to extract allicin alone. They cannot be separated completely, and the characteristic odor is unavoidable.

SUMMARY OF THE INVENTION

The present invention was completed to address the above-mentioned problems. Accordingly, it is an object of the present invention to provide a food preservative based on an odor-free vegetable alkaloid and also to provide a process for producing (extracting) such a vegetable alkaloid.

The present invention is embodied in:

(1) A food preservative which comprises water, ε-polylysine in an amount of 1~100 µg/ml, and a vegetable alkaloid extracted by ethanol.

(2) A process for producing a food preservative which comprises soaking garlic bulbs in the aqueous solution containing ethanol and phytic acid, thereby extracting allicin from the garlic bulbs, purifying the solution and adjusting its concentration, and incorporating ε-polylysine in an amount of 1~100 µg/ml with the purified solution.

(3) A process for producing a food preservative which comprises soaking garlic bulbs in an aqueous solution of ethanol, thereby extracting garlic essence, adding phytic acid therein to remove the characteristic odor of garlic, and adjusting the solution to pH 5.5~7.5.

According to the present invention, the individual constituents in the food preservative function as follows:

ε-polylysine inhibits the propagation of bacteria at concentrations as low as 1~100 µg/ml in water. It is effective for *Escherichia coli* and bacillus at a concentration of 1 µg/ml and for lactic acid bacteria at a concentration of 100 µg/ml. However, this does not hold true in the case where it is used for edible meat containing phosphate as a discoloration inhibitor, because it becomes inactive as its cationic properties are affected by the alkaline phosphate. Fortunately, the aqueous solution of the food preservative is positively charged on account of the vegetable alkaloid contained therein, so that it electrostatically acts by itself on the carboxyl groups (COOH) present on the surface layer of the bacterial cell, thereby inhibiting the cell division of bacteria. Therefore, when the food preservative is added to foods or applied to foods, the aqueous solution and ε-polylysine produce a synergistic effect in inhibiting the propagation of bacteria.

The process of the present invention requires that the essence contain phytic acid. Phytic acid acidifies the solution and acts on the enzyme alliinase contained in garlic to remove its alkylsulfonic acid anion and deactivate its enzymatic action to decompose alliin. In addition, ethanol in the solution extracts alliin from garlic. Therefore, soaking of garlic in the aqueous solution containing ethanol and phytic acid give rise to an aqueous solution in which phytic acid, ethanol, and garlic essence are mixed. When incorporated with ε-polylysine in an amount of 1~100 µg/ml, the resulting solution inhibits the propagation of bacteria owing to the synergistic effect of ε-polylysine, ethanol, and garlic essence (vegetable alkaloid). The food preservative of the present invention is quite safe because phytic acid is a substance commonly found in vegetables and is a food additive, ethanol and garlic are foods, and ε-polylysine is derived from an amino acid. In addition, it is not affected by phosphate contained in edible meat.

The process of the invention involves the soaking of garlic in an aqueous solution of ethanol (5~10%). (The amount of garlic is 50 wt % of the solution, and the duration of soaking is about 24 hours for sliced garlic or 14~30 days for bulbs.) The soaking gives rise to garlic essence. The garlic essence is incorporated with phytic acid in an amount of about 1% of its weight. After stirring and standing for about 1 hour, the garlic essence is free of the characteristic odor of garlic.

The present invention produces the remarkable effects as follows:

(a) Owing to phytic acid added at the time of garlic extraction, the food preservative is free of the characteristic odor of garlic without any loss of the ingredients of garlic. Therefore, it effectively inhibits the propagation of bacteria in foods.

(b) The garlic essence is deodorized by phytic acid, and it retains its effect unless it is heated up 50° C. and more for heat treatment. It prevents the putrefaction and poisoning of foods when it is added to or sprayed onto foods.

(c) The garlic essence incorporated with ε-polylysine can be effectively used for foods which undergo heat treatment since an antibacterial effect is obtained due to a synergistic effect produced by the combination of the garlic essence and ε-polylysine.

(d) Being made of garlic as a food, the food preservative is harmless to human bodies and available at low costs.

DETAILED DESCRIPTION OF THE PREFERRED EMBODIMENT

An embodiment of the present invention is illustrated in the following. A leaching solution was prepared from water (10,000 g), ethanol (500 g), and phytic acid (20 g). Garlic bulbs (5,000 g) were soaked in this leaching solution at room temperature (23° C.) for 14 days. With garlic bulbs removed, the leachate was filtered through filter paper. The filtrate was found to have pH 4.3 and to be free of odor. (No methyl mercaptan, ethyl mercaptan, and propyl mercaptan was detected, with the limit of detection being 0.5 ppm.) In other words, the odor concentration is less than half of that (about 1 ppm) to which human beings are sensitive. In the case of sliced garlic, soaking requires only 10~24 hours until the disappearance of odor. In addition, the duration of soaking is preferably shorter than 30 days so that the leachate does not become turbid with unnecessary substances extracted from garlic.

The garlic essence obtained by the aforesaid process was tested in the usual way for antibacterial action using Gram-positive bacteria (17 strains of 15 species and 10 genera) and Gram-negative bacteria (8 strains of 8 species and 6 genera). The results are shown in the table below.

| Organisms | MIC % (v/w) |
| --- | --- |
| E. coli | 1.27 |
| Enterotoxigenic E. coli | 1.27 |
| K. pneumoniae | 1.27 |
| E. cloacae | 1.27 |
| P. morganii | 1.27 |
| P. vulgaris | 1.27 |
| S. enteritidis | 1.27 |
| S. typhimurium | 0.61 |
| Y. enterocolitica | 0.61 |
| S. marcescens | 1.28 |
| V. mimicus | 0.63 |
| V. parahaemolyticus | 0.33 |
| V. parahaemolyticus TNK 11 | 0.61 |
| C. jejuni | 0.61 |
| P. aeruginosa | 5.3 |
| P. cepacia | 0.33 |
| P. fluorescence | 2.7 |
| S. epidermidis | 1.26 |
| S. aureus | 0.63 |
| S. agalactiae | 1.27 |
| E. faecalis | 2.7 |
| B. subtilis | 0.63 |
| B. cereus | 1.26 |
| C. perfringens | 0.63 |
| L. monocytogenes | 1.27 |

It is noted that the garlic extract is effective for *P. aernginosa*, *P. fluorescence*, and *E. faecalis* at the minimum inhibitory concentration (MIC) of 5%, 2.7%, and 2.7%, respectively. However, it is effective for other strains at an MIC in the neighborhood of 1.26% or 0.63%. This indicates that the garlic essence is effective for a large variety of poisonous bacteria and saprogens, with no significant differences among strains.

The garlic essence was tested for antibacterial action at different pH values adjusted by citric acid. It was found that the effectiveness remains unchanged at pH 6.0 and pH 7.0 but decreases as pH decreases below 6.0 or increases above 8.0. The garlic essence was also tested for effect by heat treatment. It was found that heat treatment lower than 55° C. has no effect on the antibacterial action. This result suggests that it is desirable to select proper pH values in consideration of the pH value of the food in question.

To test for preserving effect, the garlic essence was added to mayonnaise in an amount of 5 wt %. After standing at 23° C. for 13 days, the mayonnaise remained intact. As a comparative example, the mayonnaise to which no garlic essence had been added began to decay on the fifth day, with white mold growing on the upper part of the bottle.

The garlic essence was incorporated with ε-polylysine in an amount of 50 μg/ml and the resulting product was sprayed onto edible meat. The treated edible meat was allowed to stand at room temperature (23° C.) for 2 weeks. The propagation of *Escherichia coli*, bacillus, and saprogen was not observed at all.

The foregoing demonstrates that the garlic essence has antibacterial action and inhibits the propagation of bacteria even when used alone. The garlic essence, which is obtained by soaking 30~100 parts by weight of garlic in 100 parts by weight of water, should be diluted with water to give a 0.5~5% solution (to be added to foods) or a 30% solution (to be sprayed onto fish meat). In the case where the garlic essence is incorporated with ε-polylysine, the amount of the latter should be properly adjusted as follows according to microorganism in question. *Aspergillus niger* (256 μg/ml), *Candida tropicalis* (128 μg/ml), *Saccharomyces cerevisiae* (100 μg/ml), and *Streptococcus lactis* (100 μg/ml). The combination of the garlic essence and ε-polylysine produces a synergistic effect because the former is susceptible to heat whereas the latter has good heat stability (at 120° C. for 20 minutes).

In the soaking process, ethanol should be used in an amount of 5~200 parts by weight for 100 parts by weight of water. It is also possible to soak 300~1000 g of garlic in 1000 g of ethanol only for 1~30 days. A satisfactory essence will be obtained. The garlic odor can be eliminated by adding to the garlic essence phytic acid in the amount of 0.4~0.6% of garlic.

I claim:

1. A food preservative comprising an antibacterially effective amount of an ethanolic extract of garlic, a deodorizing amount of phytic acid and 1–256 μg/ml of ε-polylysine.

2. The food preservative according to claim 1, which is diluted to a 0.5–5% solution with water.

3. The food preservative according to claim 1, which is diluted to a 30% solution with water.

4. A method of producing an antibacterially effective food preservative comprising the steps of extracting garlic with ethanol at room temperature for a period of time from 10 hours to 30 days to form a garlic essence, deodorizing the garlic essence with a deodorizing amount of phytic acid and adding ε-polylysine to the deodorized garlic essence in an amount of 1–256 μg/ml.

5. The method according to claim 4, further comprising the step of adjusting the pH of the deodorized garlic essence to a value of 5.5–7.5 by the addition of citric acid.

6. The method according to claim 4, wherein the ethanol is in the form of an aqueous solution containing 5–200% by weight of ethanol.

7. The method according to claim 6, wherein the garlic is in the form of bulbs and the extracting step is carried out over a period of 14–30 days.

8. The method according to claim 6, wherein the garlic is in the form of slices and the extracting step is carried out over a period of 10–24 hours.

9. The method according to claim 6, wherein the phytic acid is present during the extracting step in an amount of 0.4 to 0.6% by weight of the garlic.

10. The method according to claim 6, wherein the phytic acid is added after the extracting step in an amount of 1% by weight of the garlic essence.

* * * * *